US012603176B2

(12) United States Patent
Sommer et al.

(10) Patent No.: US 12,603,176 B2
(45) Date of Patent: Apr. 14, 2026

(54) AUTOMATED GENERATION OF MEDICAL TRAINING DATA FOR TRAINING AI-ALGORITHMS FOR SUPPORTING CLINICAL REPORTING AND DOCUMENTATION

(71) Applicant: Smart Reporting GmbH, Munich (DE)

(72) Inventors: Wieland Sommer, Munich (DE); Sigrid Auweter, Puchheim (DE)

(73) Assignee: SMART REPORTING GMBH, Munich (DE)

( * ) Notice: Subject to any disclaimer, the term of this patent is extended or adjusted under 35 U.S.C. 154(b) by 151 days.

(21) Appl. No.: 18/021,151

(22) PCT Filed: Aug. 14, 2020

(86) PCT No.: PCT/EP2020/072922
§ 371 (c)(1),
(2) Date: Feb. 13, 2023

(87) PCT Pub. No.: WO2022/033706
PCT Pub. Date: Feb. 17, 2022

(65) Prior Publication Data
US 2023/0326598 A1    Oct. 12, 2023

(51) Int. Cl.
*G16H 50/20*        (2018.01)
*G16H 15/00*        (2018.01)
*G16H 30/40*        (2018.01)

(52) U.S. Cl.
CPC ............. *G16H 50/20* (2018.01); *G16H 15/00* (2018.01); *G16H 30/40* (2018.01)

(58) Field of Classification Search
CPC ........ G16H 15/00; G16H 30/40; G16H 50/70; G16H 10/60; G16H 30/00
See application file for complete search history.

(56) References Cited

U.S. PATENT DOCUMENTS

2013/0070986 A1    3/2013  Peleg et al.
2019/0096060 A1    3/2019  Zhang et al.
(Continued)

FOREIGN PATENT DOCUMENTS

EP          3432313 A1       1/2019
WO        2016135100 A1       9/2016
WO      WO-2022036351 A1 *    2/2022    ........... A61B 5/7267

OTHER PUBLICATIONS

Martin J., et al. "Preparing medical imaging data for machine learning." Radiology 295.1 (2020): 4-15. (Year: 2020).*
(Continued)

*Primary Examiner* — Jason B Dunham
*Assistant Examiner* — Constantine Siozopoulos
(74) *Attorney, Agent, or Firm* — QUARLES & BRADY LLP

(57)        ABSTRACT

A computer-implemented method, computer-system and computer-program product for generating medical training data for training artificial-intelligence (AI) algorithms for supporting clinical reporting and documentation are described. To generate the training data medical image data of a patient comprising medical image data elements are received and a medical findings report is generated, edited and/or received that summarizes individual medical findings. It comprises machine-readable findings-report elements the contents of which comprise semantic features. The contents of the findings report elements are automatically assigned to unique identifiers, wherein each identifier uniquely represents the medical semantic content of exactly one individual medical finding. The medical image data are annotated by linking one or more medical image data elements to the unique identifiers of one or more contents of the findings-report elements, and the annotated received medical image data are stored as training data for AI
(Continued)

101 — receiving medical image data of a patient

102 — generating, editing and/or receiving a medical findings report on the patient 103 — automatic assigning the respective findings-report element-content to unique identifiers 104 — annotating the received medical image data by linking one or more medical image-data elements to the unique identifiers of one or more contents of the findings-report elements 105 — storing the annotated received medical image data as training data for AI algorithms for supporting clinical reporting and documentation algorithms for supporting clinical reporting and documentation.

20 Claims, 8 Drawing Sheets

(56)                    References Cited

U.S. PATENT DOCUMENTS

| | | | |
|---|---|---|---|
| 2019/0188848 A1 | 6/2019 | Madani et al. | |
| 2020/0160967 A1* | 5/2020 | Lyman | G06T 7/0012 |
| 2020/0160970 A1 | 5/2020 | Lyman et al. | |
| 2020/0211692 A1 | 7/2020 | Kalafut et al. | |
| 2022/0005565 A1* | 1/2022 | Lyman | G16H 15/00 |

OTHER PUBLICATIONS

Edlund, What is Synoptic Reporting?, https://www.softworksgroup.com/synoptec-blog/what-is-synoptic-reporting/, Jan. 6, 2014, 4 pages.

PCT International Search Report and Written Opinion, PCT/EP2020/072922, Apr. 13, 2021, 14 pages.

International Search Report and Written Opinion for International Application No. PCT/EP2020/072922 dated Apr. 13, 2021 (14 pages).

Edlund, Tim, "What is Synoptic Reporting?—Softworks Group," Jan. 6, 2014, XP055792127, URL:https://www.softworksgroup.com/synoptec-blog/what-is-synoptic-reporting/ [Retrieved from the Internet Feb. 14, 2023].

European Patent Office, Examination Report for corresponding EP Patent App. No. 20758153.9, dated Feb. 2, 2026 [7 pgs.].

Wolf et al., "The Medical Imaging Interaction Toolkit", Medical Image Analysis, vol. 9, No. 6, May 17, 2005 (May 17, 2005), pp. 594-604, XP093358045, GB ISSN: 1361-8415, DOI: 10.1016/j.media.2005.04.005 [11 pgs. ].

Cheng et al., "Annotate, Build, and Adapt Models for Medical Imaging with the Clara Train SDK NVIDIA Technical Blog", Jun. 26, 2019 (Jun. 26, 2019), pp. 1-12, XP093358053, Retrieved from the Internet: URL:https://developer.nvidia.com/blog/annotate-adapt-modelmedical-imaging-clara-train-sdk/ [12 pgs. ].

* cited by examiner

FIG. 1

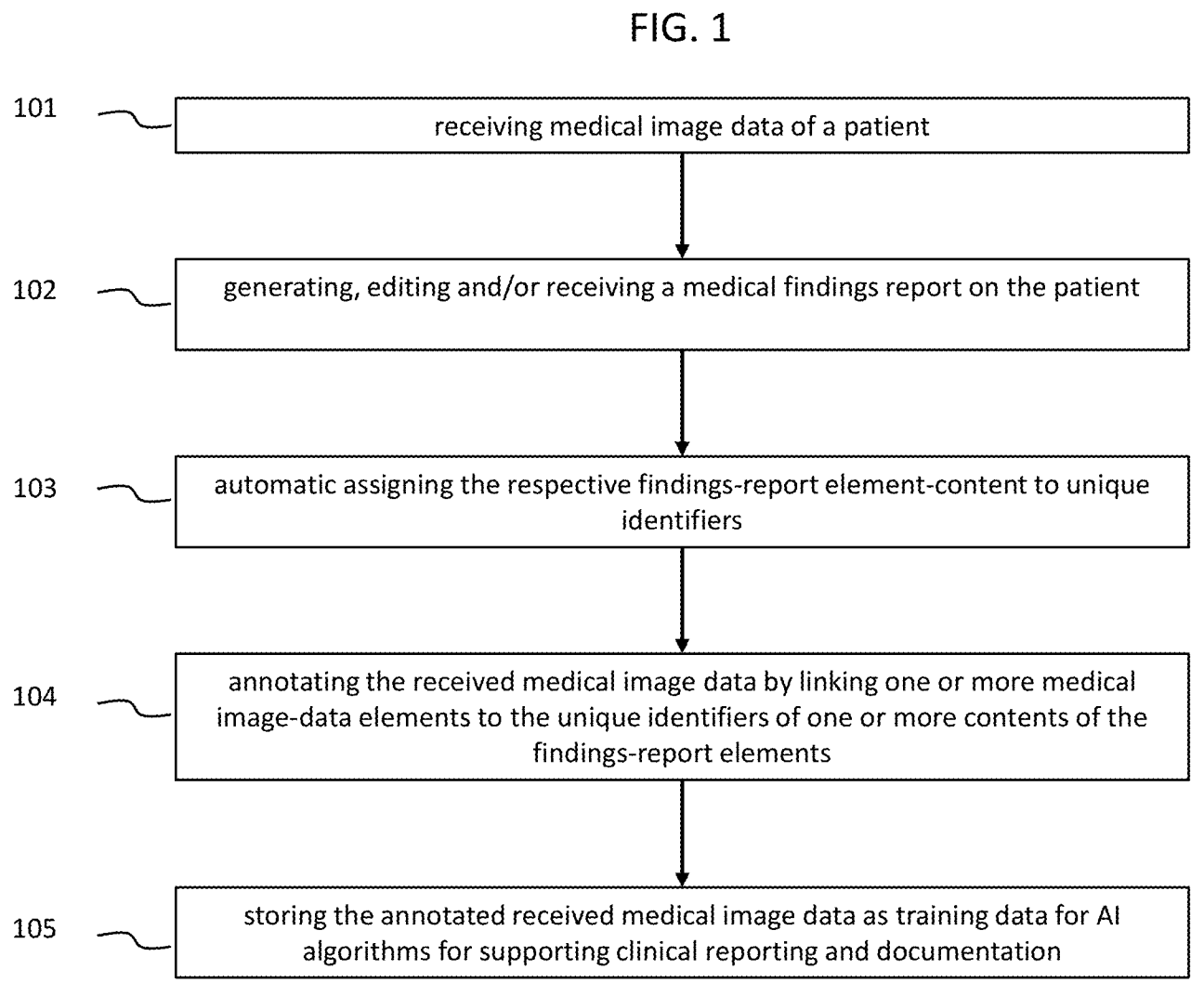

101 — receiving medical image data of a patient

102 — generating, editing and/or receiving a medical findings report on the patient 103 — automatic assigning the respective findings-report element-content to unique identifiers 104 — annotating the received medical image data by linking one or more medical image-data elements to the unique identifiers of one or more contents of the findings-report elements 105 — storing the annotated received medical image data as training data for AI algorithms for supporting clinical reporting and documentation

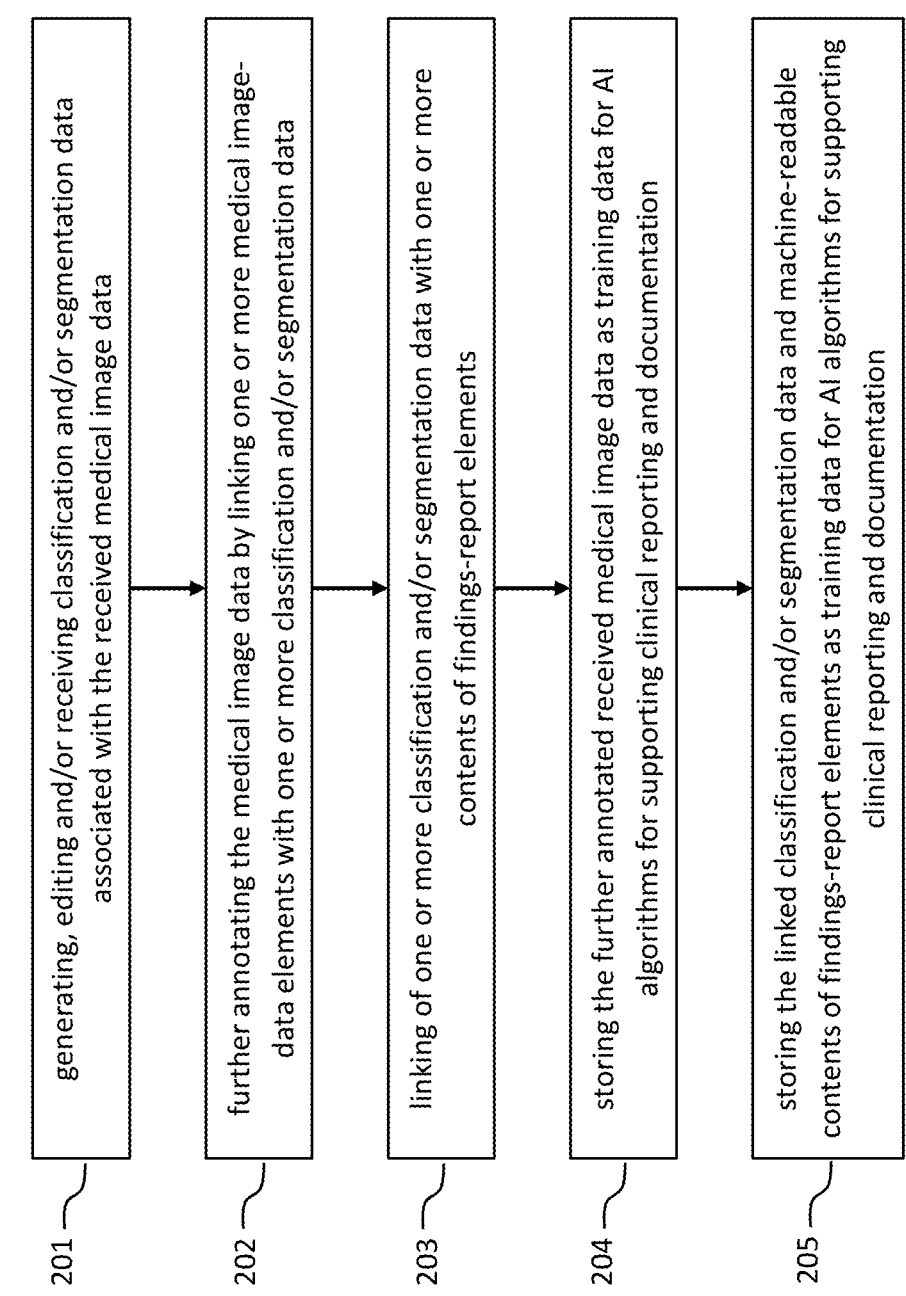

201 — generating, editing and/or receiving classification and/or segmentation data associated with the received medical image data 202 — further annotating the medical image data by linking one or more medical image-data elements with one or more classification and/or segmentation data 203 — linking of one or more classification and/or segmentation data with one or more contents of findings-report elements 204 — storing the further annotated received medical image data as training data for AI algorithms for supporting clinical reporting and documentation 205 — storing the linked classification and/or segmentation data and machine-readable contents of findings-report elements as training data for AI algorithms for supporting clinical reporting and documentation

FIG. 7

AUTOMATED GENERATION OF MEDICAL TRAINING DATA FOR TRAINING AI-ALGORITHMS FOR SUPPORTING CLINICAL REPORTING AND DOCUMENTATION

CROSS-REFERENCE TO RELATED APPLICATIONS

This application is a U.S. national phase application of pending International Patent Application No. PCT/EP2020/072922, which was filed on Aug. 14, 2020, and is now published as WO 2022/033706 A1. The disclosure of this patent application is incorporated herein by reference in its entirety for all purposes.

This invention relates to the field of generating medical training data for training AI algorithms for supporting clinical reporting and documentation.

BACKGROUND OF THE INVENTION

Algorithms for automatic analysis and diagnostic decision support play an increasingly important role in medicine and in particular in the field of medical imaging. They support medical professionals in reporting, e.g. by making a pre-selection of possibly relevant images or even by making suggestions for reporting and diagnosis. This can reduce the number of errors in reporting, and automate and accelerate the reporting process itself.

Especially algorithms based on artificial intelligence (AI) are well-known and promising candidates for automated support of medical imaging and diagnosis. Such AI algorithms must first be trained using training data. The training data should represent typical clinical use cases and should as well as possible statistically represent the patient population.

For the training of AI algorithms for the automatic analysis of medical images, image data provided with annotations and/or labels are required. Such annotated images may also be necessary for the training of algorithms for diagnostic decision support In the context of AI training, the terms labels and annotations are used. For better understanding, and readability, both terms will be subsumed under the term annotation in this text, such that the term annotation refers to labels and/or annotations.

In this context, annotations are attributes that are linked to the images during medical evaluation. They typically include classification and segmentation information. Classification information arranges the images or certain structures or areas in the images into categories such as tumor vs. cyst, determination of a risk score, etc. Segmentation information allows related image structures such as organs, tissue types, blood vessels, cells and areas affected by a specific pathology to be recognized and if necessary, distinguished from other image structures. The AI algorithms trained in this way can then automatically and autonomously perform the classification and/or segmentation of images.

For example, the first step in classification is to extract effective image features from the image. The second step is then, for example, to create models using the image features to classify the image data set.

In principle, however, annotations can also contain further information about the patient or his or her images. Such information could, for example, be taken from the patient's file and findings reports and describe the diagnosis or health status of the patient in a more extensive way than the segmentations and classifications. In this document, such information is referred to as semantic features.

Typically, annotations are the limiting factor in the development of image-based algorithms. They are usually not obtained from clinical routine. Rather, data sets for AI training are recorded specifically for this purpose. Typically, the annotations are then created manually by trained personnel. In some approaches, annotation is also performed automatically using algorithms (e.g. automatic image segmentation, automatic extraction of semantic features via natural language processing (NLP).

The creation of training data sets in this manner is complex and time-consuming. The data must be acquired or selected, the technical personnel must be trained and assigned to annotate, and finally the annotations must be created, reviewed and supervised.

In addition, such training is based on selected data sets that may not reflect the specifics of individual diseases, certain patient groups or device-specific differences in the existing measurement systems. The algorithms trained in this way could therefore not reflect the typical use cases sufficiently well. In fact, it is even possible to introduce a training data-based bias in this way.

Especially with regard to the regulatory approval of such algorithms as medical devices, it is even more important to use only such training data that are statistically representative, ethically sound and ideally even quality-assured. Since the training of AI algorithms also requires very large amounts of training data, the provision of sufficient data that meet the discussed criteria is a great challenge.

In US 2013/0070986 A1 it is therefore proposed to further train already trained computer aided diagnosis (CAD) algorithms using clinical image data. For this purpose, unclassified data is given to a health professional for classification and then added to the existing training data. The classification information can be generated dynamically while viewing the data.

EP 3432313 A1 also proposes the updating of training data. For this purpose, user feedback on the training data is iteratively requested via a user interface and the training data is updated based on this feedback.

Finally, AI algorithms trained on training data the annotations of which contain only segmentation and classification information are able to automatically perform classification and segmentation tasks. In principle, however, by adding further semantic features to the annotations AI algorithms for many other clinical tasks can be trained.

Against this background it is desirable to further improve the training data for AI algorithms for supporting clinical reporting and documentation as well as the generation of such training data.

SUMMARY OF THE INVENTION

The invention provides a method, a system and a computer program product for improving the training data for AI-algorithms for supporting clinical reporting and documentation as well as the generation of such training data.

One aspect of the invention concerns computer-implemented method for generating medical training data for training artificial-intelligence (AI) algorithms for supporting clinical reporting and documentation according to independent claim 1.

Another aspect of the invention concerns a computer system for generating medical training data for training artificial intelligence (AI) algorithms for supporting clinical reporting and documentation according to independent claim 8.

Another aspect of the invention concerns a computer-program product for generating medical training data for training artificial intelligence (AI) algorithms for supporting clinical reporting and documentation according to independent claim 15.

Based on these and the following aspects and embodiments of the invention, annotations can be automatically linked to the medical image data. The annotations can be obtained directly and automatically from routinely generated findings reports and other data generated in daily hospital routine. Since the associated image data is generated in the course of the usual medical workflow, the data sets are automatically generated in the process of regular clinical routine. Therefore, both the image data and the diagnostic reports also meet clinical quality assurance standards. Consequently, quality-assured training data can be automatically generated during ongoing clinical practice—ideally in the background, i.e. without changing the routines of the clinical staff.

In addition, these data automatically comprise for each facility typical clinical use cases as well as device-specific characteristics and represent statistically the typical patient population. The system can therefore be used to initially develop and/or train algorithms adapted to the respective region/hospital/etc. and/or to adapt them by re-training (feedback training). Furthermore, existing algorithms can be validated.

The generated data sets (images+annotations) are suitable for the training of diagnostic algorithms in general, especially AI algorithms. Because much more than just segmentation and classification information is used as annotations, algorithms can be trained for other tasks than conventional automatic segmentation and classification of image data. The potentially trainable algorithms include, e.g., algorithms for the detection of lesions, algorithms for automatic quantification of medical images (e.g. coronary calcium scoring on CT images), algorithms for patient triage, algorithms for the automation of decisions or the automated generation of decision proposals, algorithms for the support or even generation of diagnoses, up to algorithms for the automatic generation of finding reports from all available clinical data. Thus, such algorithms can support many aspects of clinical reporting and documentation. In general, the algorithms can be derived from data by recognizing patterns and rules in the data (as generally in machine learning). Therefore, the annotations used to train the algorithms can also determine the potential output of the algorithms or even be the output itself. In other words, the functionality and output of an AI algorithm depend on the data and in particular the annotations that are used to train them. Therefore, adding or using new data and annotations when training AI algorithms can lead to new functionalities and applications of the resulting algorithms.

The above and other advantages result from the following considerations, where aspects and embodiments of the invention are discussed and, where appropriate, reference is made to the corresponding drawings, which show preferred embodiments of the invention for illustration purposes. However, these embodiments do not necessarily represent the full scope of the invention.

BRIEF DESCRIPTION OF THE DRAWINGS

FIG. 1 illustrates exemplary steps according to the invention for the generation of AI training data for supporting clinical reporting and documentation;

FIG. 1*a* shows an example of medical image data comprising medical image data elements;

FIG. 2 illustrates exemplary steps according to the invention to include segmentation and/or classification data into the generation of AI training data for supporting clinical reporting and documentation;

FIG. 7 illustrates an example of how to link the images-, findings report- and segmentation/classification-data.

DETAILED DESCRIPTION

Figure 3:
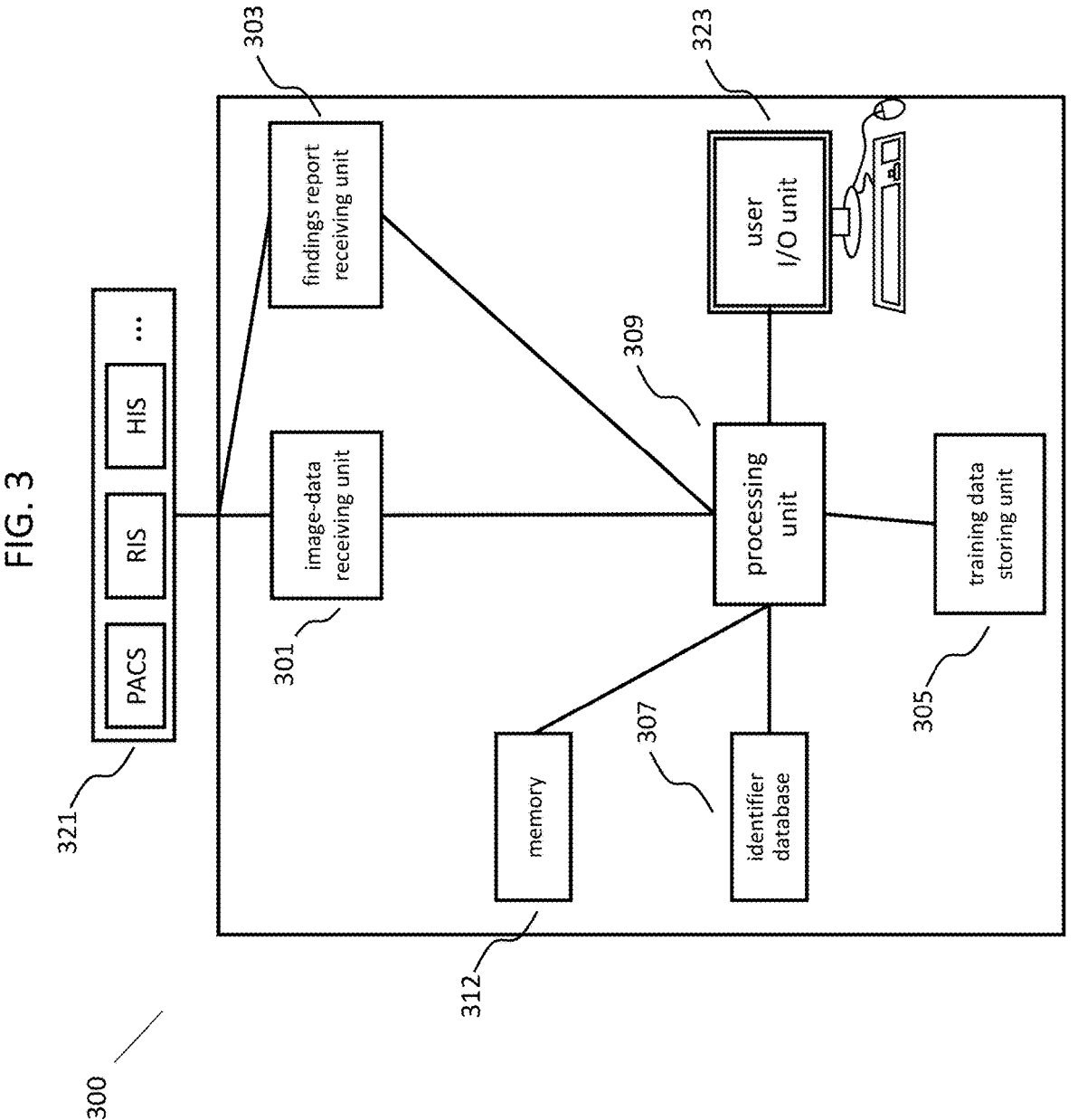
FIG. 3 shows exemplarily and schematically a computer system according to the invention for the generation of AI training data for supporting clinical reporting and documentation.

FIG. 1 schematically shows the steps of a method according to the invention for the generation of training data for algorithms for supporting clinical reporting and documentation. The user, typically a radiologist or other physician, is in a first step 101 provided with medical image data. Medical image data can be anatomic and/or anatomic-functional image data, i.e. show anatomical structures, possibly in combination with dynamic and/or functional processes such as, e.g. flow, perfusion, diffusion or contrast agent enhancement. Typically such data are acquired using typical image modalities such as X-rays, computed tomography (CT), Single Photon Emission Computed Tomography (SPECT), positron emission tomography (PET), super-conducting quantum interference device (SQUID), magnetic resonance tomography (MRI), functional MRI (fMRI), ultrasound (US) or optical coherence tomography (OCT). Of course, image data generated by hybrid modalities such as MR-PET or PET-CT can also be considered. In addition, image data from pathology such as digital pathological cuts as well as from ophthalmology such as ophthalmoscopy may also be used.

Such image data sets usually comprise one or more individual 2D or 3D images. The individual images that can be displayed with these data sets correspond, for example, to the individual slices in tomographic procedures. The images can therefore be available as series (3D slice imaging) or as individual images. In addition, the images can form a temporal series (3D or 4D data), and, for example, reproduce dynamic processes, e.g. the temporal accumulation of a contrast agent, the growth of a tumor or temporal courses of neuronal signals. In particular, the images can also be part of a video.

It is also possible that such image data sets are composed of images from different modalities mentioned above: for example, a data set with MRI images of the prostate and the corresponding digital microscope images from the pathologist.

Medical image data can, however, also be non-anatomic image data, i.e. not show anatomical structures but be other visually assessable medical data that visualize measured signals, e.g., in form of electrocardiograms (ECG), electro-encephalograms (EEG), cardiotocograms (CTG) or audio-grams.

In any case, the contents of the images are formed by image elements. In principle, image elements can be single or multiple pixels or voxels. Examples of image elements are the depicted individual organs or other coherent tissue. Pathological areas such as cysts, tumors or altered tissue areas are further examples. Other examples of possible image elements are vascular trees or sections thereof, as well as body fluids such as blood, cerebrospinal fluid, lymphatic fluid or urine. Image elements can also be regions or volumes of interest (ROIs or VOIs), i.e. groups of pixels or voxels that have been marked manually by a user or auto-matically by software.

Figure 1A:
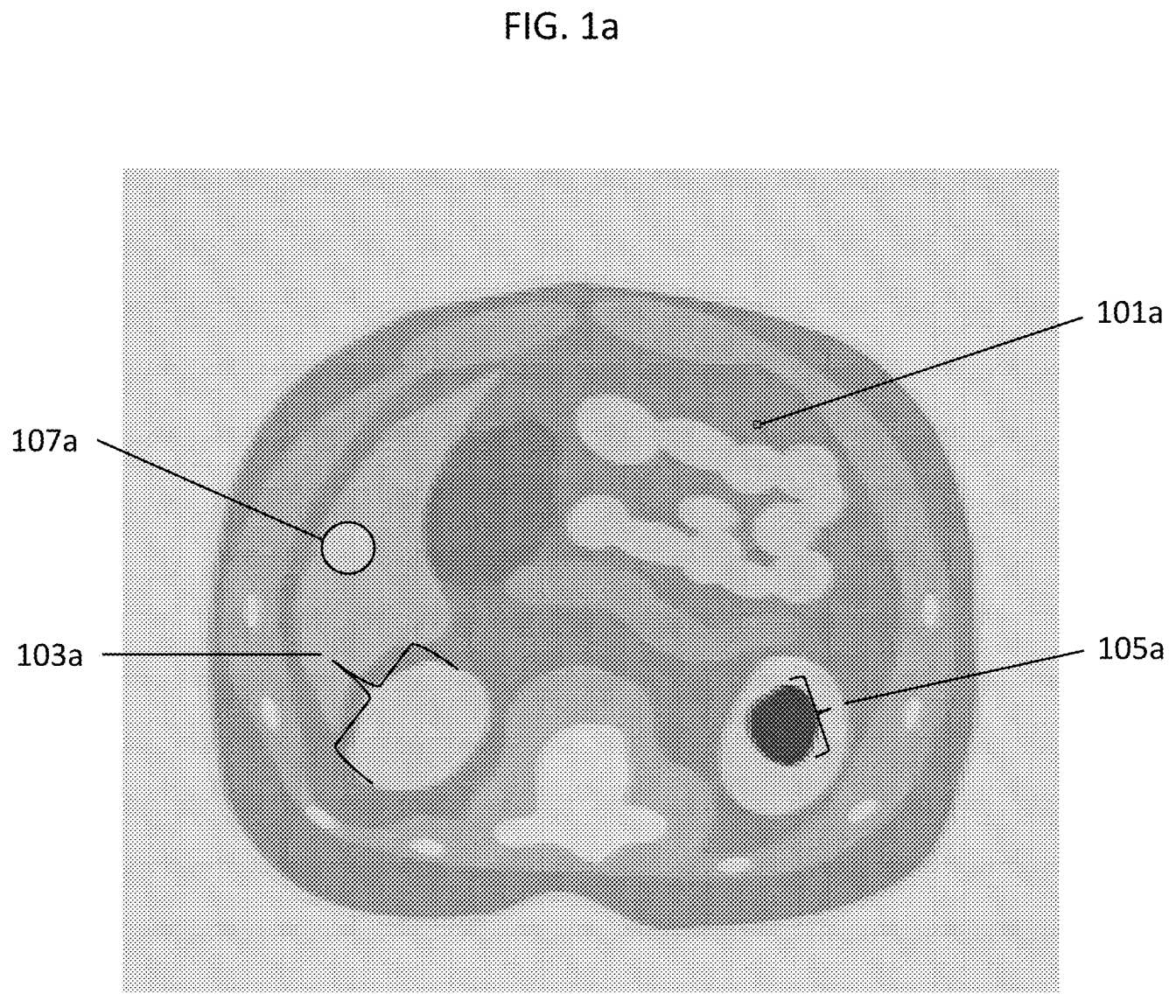

FIG. 1a illustrates image data elements using the example of a tomographic slice of a human torso. E.g., image element 101a is an individual pixel/voxel of the image slice, image element 103a is an individual organ shown in the image slice, image element 105a is a pathologic area in an organ shown in the image slice and image element 107a is an ROI defined in the image slice.

The medical image data about a patient are loaded and made available to the user and/or, if necessary, to supporting algorithms, e.g. for computer-aided diagnosis (CADx) or detection (CADe).

The medical image data and eventually other medical data like laboratory findings, pathological findings, medical let-ters, personal data, other patient data or other elements of an electronic health record (EHR) may either be sent by or retrieved from electronic data archiving systems. In particu-lar these may be databanks and repositories, like a picture archiving and communication system (PACS), a radiology information system (RIS), and/or a hospital information system (HIS).

In an additional step 102, a medical report belonging to the medical data is received by the user, e.g., sent by or retrieved from a database or repository as the ones discussed above. However, the report can also be created by the user, if necessary, with the help of supporting algorithms. A loaded medical report can also be revised and edited by the user or a software. For example, incorrect information can be removed or corrected and information not yet available can be added, i.e., the report can be extended. The findings report can also be converted into another format. In the case that the findings report is a modular findings reports, new mod-ules may be added.

The medical findings reports used can, in particular, be machine-readable. In particular, the findings reports can be constructed from findings report elements.

For example, the findings reports can be structured. Structured reports are based on structured, machine-readable reporting templates that can be progressively filled in by a user. Ideally, a structured report is machine-readable, has a fixed structure and contains standardized elements, wording and layout. In addition, pre-generated report templates can be used. These may provide case-specific structure and include recommended reporting steps. For example, WO 2016/135100 A1 describes an approach to provide structured reports, which proposes the use of report modules as report building blocks based on decision trees. These are based on a hierarchical tree structure that also reflects dependencies of information. The resulting medical report is created in a modular fashion, in that medical report modules can be added step-by-step during the creation of the medical report. The described findings reports comprise semantic fea-tures. Semantic features can be derived partly from segmentations/classifications. One segmentation/classification can be related to one or more semantic features, or several segmentations/classifications can be related to one semantic feature. Usually, however, the semantic features contain considerably more elements and describe the diagnosis or health status of the patient in a more comprehensive manner than the segmentations and classifications.

If the findings reports are created or edited, the corre-sponding images can be analyzed automatically or manually, or a combination of both. The results of the analysis (e.g. segmentations, classifications and/or semantic features) can also be further adjusted manually, for example. The results are then transferred in full to the findings report. This can be done manually and/or automatically. The findings report can also be modified and/or extended manually and/or automati-cally. In an exemplary execution, the user must first release the findings before they are stored.

Some embodiments also provide a user interface that allows the user to accept, reject or adjust the results of automatic image evaluation.

The elements of the findings report or their contents can in a further step 103, e.g., also be automatically linked with unique identifiers, e.g. by a software tool. This means that these unique identifiers are assigned to the terms contained in the findings report elements. For example, an identifier can be any form of terminology or code that can be uniquely assigned to the content. Each identifier stands uniquely for a specific meaning, i.e. a medical semantic content. Several terms or words, which e.g. are synonymous in the sense that they share a specific meaning, can then be assigned to a single, specific identifier, which is uniquely assigned to the specific meaning. For example, besides the term glioblas-toma multiforme, the terms GBM or astrocytoma WHO grade IV are commonly used for the same medical finding. In addition, a German radiologist might term this finding Astrozytom (WHO Grad IV). However, to all four terms that can be subsumed under the same medical meaning or definition, a unique identifier can be assigned, which stands for exactly this one medical meaning.

According to some embodiments, such identifiers are certain technical terms or elements of a controlled termi-nology in particular elements of a lexicon, standard, or a medical ontology like RadLex, SNOMED-CT, LOINC or DICOM. Such lexicons assign both a unique identification code and a term definition and, if necessary, synonyms and acronyms to the individual terms. The use of such codes, e.g., makes it possible to search for individual terms within a finding. Using such lexicons, enables an automated evalu-ation of the findings. Also, multilingual, but semantically identical findings can be used by the findings authors independent of the language used. The codes are, for example, letter codes or numeric or alphanumeric codes.

Such encoded finding reports are also known as synoptic reports. A synoptic report is a medical findings report in which the individual findings elements are assigned to concrete database entries. Synoptic findings are completely machine-readable and the individual findings elements can be uniquely assigned a meaning Electronic synoptic findings reports use templates with coded values to record interop-erable data in discrete fields. Synoptic findings provide semantic features.

In some embodiments, the unique identifiers, e.g. of step 103, comprise unique identification codes.

In some embodiments, the unique identifiers, e.g. of step 103, originate from a unique medical ontology.

For example, an ontology like RadLex may be used to generate the synoptic report. In addition to providing the functionality of above discussed lexicons, an ontology not only defines the radiological terms but also the interdependencies and relations of the terms. Thus, relationships between terms can be mapped and put into context. An ontology can thus also capture the meaning of what is expressed. Corning back to the above example of the term glioblastoma multiforme, the terms glioblastoma multiforme, GBM, astrocytoma WHO grade IV and even Astrozytom (WHO Grad IV) are specified by the code "RID4044" by RadLex and further a definition of the term is provided. In a further example a combination of several private and/or standard ontologies is used.

In some embodiments, the medical findings report of step 102 is a synoptic structured medical findings report.

In a further step 104, the contents of selected findings report elements are linked to the image data sets described above. These linked data serve as training data for AI algorithms for supporting clinical reporting and documentation and are stored in an additional step 105.

In some embodiments, the images or image elements are also linked to the unique identifiers. The contents of the elements of the findings report can then be linked to the image data sets or their images and/or image elements via these unique identifiers.

The entire image data set, individual images of the image data set, such as one or more slices, or individual image elements within an image or slice can be linked to the contents or partial contents of one or more findings report elements. Such a linking is also called annotating the image data.

As discussed above, annotations derived from a findings report can but do not have to contain segmentation and/or classification information. Thus, in the case that there are one or more findings-report element-contents that are linked to the received medical image data, it is possible that none of them contains segmentation or classification information. Furthermore, in some embodiments, the contents of the one or more findings report elements used for annotating the one or more medical image data elements comprise information in addition to and/or other than classification and/or segmentation information. Thus, it is possible that during the linking of one or more predefined findings-report element-contents with the received medical image data in step 104 no classification and segmentation information is linked.

According to some embodiments, the linking of the medical image data with the identifiers of one or more findings-report element-contents in step 104 is carried out while the medical findings report element is generated or edited. In other words, the described annotation can be carried out online, i.e. dynamically during reporting on the images and/or the creation of the report. In other embodiments, the linking is carried out after the generation of a findings report or using a loaded, preexisting findings report.

According to other embodiments, the described annotating can take place in a step following the creation of the finding report, in particular on the basis of a loaded, preexisting findings report.

Contents of the findings reports or findings report elements, which are in principle considered for linking with the images and/or image elements, or segmentation and/or classification data, can be determined in advance or during the creation of the report. The finding report contents can thus be predetermined. Such a selection can be based, for example, on guidelines, textbooks or general recommendations. Additionally, or alternatively, the selection can also be made freely by a user, e.g. based on experience or study guidelines. Finally, the selection can also be based on requests or specifications from those responsible for training or retraining of AI algorithms.

As described in the introduction, the annotations of image data used for training AI algorithms usually consist of classification and segmentation data created specifically for this purpose. Segmentation and classification information includes, for example, organ segmentation, segmentation of lesions, positions of lesions, texture analysis, quantification of tissue/organ volumes, planning of surgical or interventional procedures, classification of lesions (benign vs malignant, morphological subtypes, tumor staging), and others.

According to some embodiments, such classification and segmentation data can also be loaded or newly generated by the user, if necessary, with the help of supporting algorithms. Furthermore, such classification and segmentation data can be loaded and, if necessary, be revised and edited by the user or a software. This is illustrated in FIG. 2.

Therefore, some embodiments comprise carrying out the following additional steps e) 201 generating, editing and/or receiving classification and/or segmentation data comprising classification and/or segmentation information associated with the received medical image data and/or the patient, and f) 202 further annotating the medical image data by linking one or more medical image-data elements with one or more classification and/or segmentation data, and/or g) 203 linking of one or more classification and/or segmentation data with one or more contents of findings-report elements, and h) storing as training data for AI algorithms for supporting clinical reporting and documentation
   204 the further annotated received medical image data, and/or
   205 the linked classification and/or segmentation data and machine-readable contents of findings-report elements.

In some embodiments, the segmentation and/or classification data can be linked to the unique identifiers. The segmentation and/or classification data can then be linked to the contents of the findings report elements and/or the image data sets, images, and/or image elements via these identifiers.

Thus, in some embodiments, linking of one or more predefined findings-report element-contents, received image data and/or classification and/or segmentation data in the steps 104, 202 and/or 203 is carried out via the unique identifiers. Furthermore, it is possible to save only the identifiers instead of the contents of the findings-report as annotations.

In general, by using the described methods, new sets of training data can be generated from scratch or existing sets of training data can be updated, be it by extending, tuning or retraining them. Thus, in some embodiments, an existing set of training data for AI algorithms for supporting clinical reporting and documentation is updated with the annotated received medical image data.

Furthermore, reports that already use unique identifiers, e.g., synoptic structured reports, but were not yet used for annotating medical image data as in the described embodiments can retrospectively be used to annotate the corresponding image data. Thus, even older finding reports and their image data can be used to generate AI training data at a later stage.

The AI algorithms trained by using training data a created by the methods, systems and computer program products described in this text can support clinical reporting and documentation in many aspects and fields. E.g., in some embodiments, the AI algorithms are adapted to support radiological and/or pathological reporting and documentation FIG. 3 schematically shows a computer system according to one aspect of the invention. Medical image data and medical findings reports, such as those described in connection with the methods discussed above, can be retrieved via an image-data receiving unit 301 and a findings-report receiving unit 303 from a data repository or server 321, such as a PACS, RIS or HIS.

The system further comprises a processing unit 309 that can consist of one or more processors and/or processor cores. Depending on the respective embodiment, the processing unit 309 is capable of carrying out all the process steps described in connection with the exemplary methods discussed above.

The system further comprises a training data storing unit 305 where training data can be stored, e.g. on one or more hard drives, cloud or local servers, CDs or DVDs or flash memories.

For this purpose, the processing unit 309 can be set up to display the received image data in a user input/output (10) unit 323 and, if necessary, to make them processable by means of appropriate software and via appropriate interfaces, to retrieve and/or receive medical reports via the findings-report receiving-unit 303, to edit existing reports and/or create new reports, as described in the context of the exemplary embodiments discussed above, to display, via the user input/output (10) unit 323, the diagnostic reports as well as the interfaces necessary for their presentation, processing or creation, and/or to have access to an identifier database 307 which contains, for example, the controlled terminologies, lexicons and/or ontologies described in connection with the methods discussed above.

The processing unit 309 is further setup to link the contents of the finding reports and/or finding report elements to identifiers comprised in the accessible identifier database 307. In some embodiments, the processing unit links the unique identifiers of the identifier database 307 also to the image data sets, images and/or image elements. Thus, both the contents of the findings reports/findings report elements and image data sets, images and/or image elements are linked to each other via these identifiers.

According to some embodiments, the unambiguous identifiers of the identifier database 307 comprise at least one of unique identification codes, and/or originate from a unique medical ontology.

According to some embodiments, the processing unit 309 is further configured to generate, edit and/or receive synoptic structured medical findings reports.

According to some embodiments, the contents of the findings-report elements used for annotating the one or more medical image data elements comprise information in addition to and/or other than classification and/or segmentation information.

Figure 4:
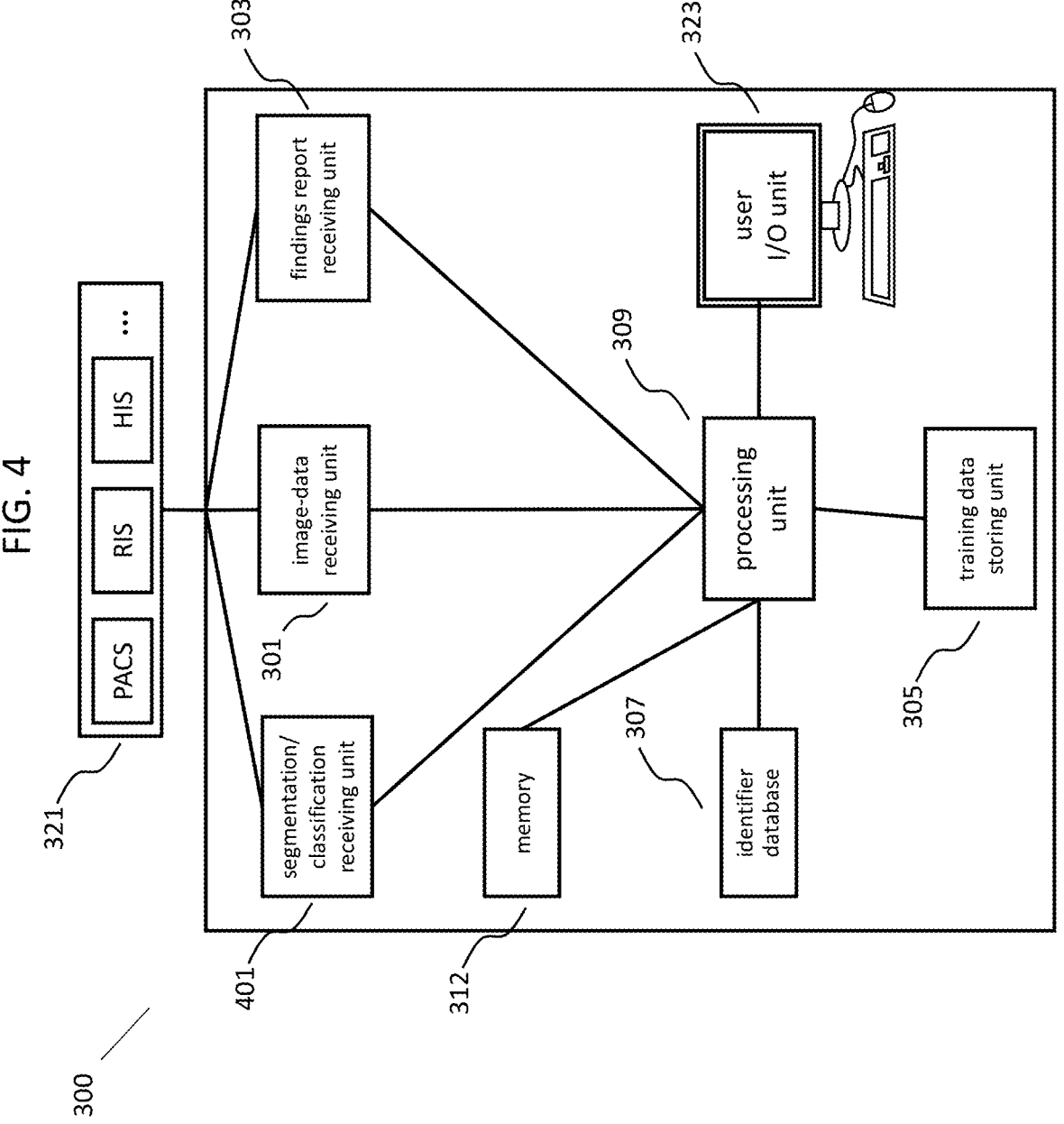
FIG. 4 shows exemplarily and schematically a computer system according to the invention for including segmentation and/or classification data into the generation of AI training data for supporting clinical reporting and documentation.

FIG. 4 schematically shows an embodiment of the invention, where the system also comprises a segmentation and classification data receiving unit 401 configured receive classification and/or segmentation data associated with the received medical image data which, potentially, are not contained in the medical findings report. The processing unit is in this example further configured to a. generate, edit and/or, via the segmentation and classification data receiving unit, classification and/or segmentation data comprising segmentation and/or classification information associated with the received medical image data and/or the patient, b. annotate the received medical image data by linking one or more medical image data elements with the classification and/or segmentation data, and/or c. link one or more of the classification and/or segmentation data with one or more of the contents of findings-report elements, and d. store as training data for AI algorithms for supporting clinical reporting and documentation the further annotated received medical image data, and/or the linked classification and/or segmentation data and contents of findings-report elements.

Examples of the segmentation data and/or classification data are described in connection with the methods discussed above. The segmentation and classification data can, e.g., be retrieved via the segmentation/classification receiving unit 401 from a data repository or server, such as a PACS, RIS or HIS.

According to some embodiments, such classification and segmentation data can also be loaded or newly generated by the user, if necessary, with the help of supporting algorithms. Furthermore, such classification and segmentation data can be loaded and, if necessary, be revised and edited by the user or a software.

Thus, in some embodiments, an existing set of training data for AI algorithms for supporting, clinical reporting and documentation is updated with the annotated received medical image data. This has already been discussed above in the text in connection with the relevant method examples.

Some embodiments further comprise a memory 312 where the information is stored, which contents of the findings reports and/or findings report elements can be linked to medical data such as images, and/or image elements. The memory 312 can in addition contain information on which contents of the findings reports and/or findings report elements can be linked to segmentation and/or classification data. Finally, the memory 312 can also store information on which medical data such as images, and/or image elements can be linked to segmentation and/or classification data. Based on this information the linking can be performed automatically, i.e. without requiring any input by a user. As discussed above, such a selection can be based, for example, on guidelines, textbooks or general recommendations. Additionally, or alternatively, the selection can also be made freely by a user, e.g. based on experience or study guidelines. Finally, the selection can also be based on requests or specifications from those responsible for training or retraining of AI algorithms. The memory 312 can be any device suitable for storing, information. E.g., it can be a hard-drive or be integrated into one, it can be a RAM or a ROM. It may be a fixed component of a device or removable e.g. like a USB flash drive.

According to some embodiments, the processing unit 309 is further configured to link the medical image data and the one or more predefined findings-report element-contents while the medical findings report element is generated or edited. As discussed above, the linking can then be carried out dynamically while generating a findings report or in a subsequent step.

In addition, the processing unit 309 stores the linked one or more findings-report element-contents and received medical image data in the training data storing unit 305 as training data for AI algorithms for supporting clinical reporting and documentation. The training data storing unit 305 can comprise one or more data storage devices, e.g., solid-state drives (SSD) and/or hard-disk drives (HDD). Furthermore, the training data storing unit 305 can be a local data storage. Furthermore, the training data storing unit 305 can be on a server and can, e.g., be organized as a repository.

Figures 5A, 5B, 5C:
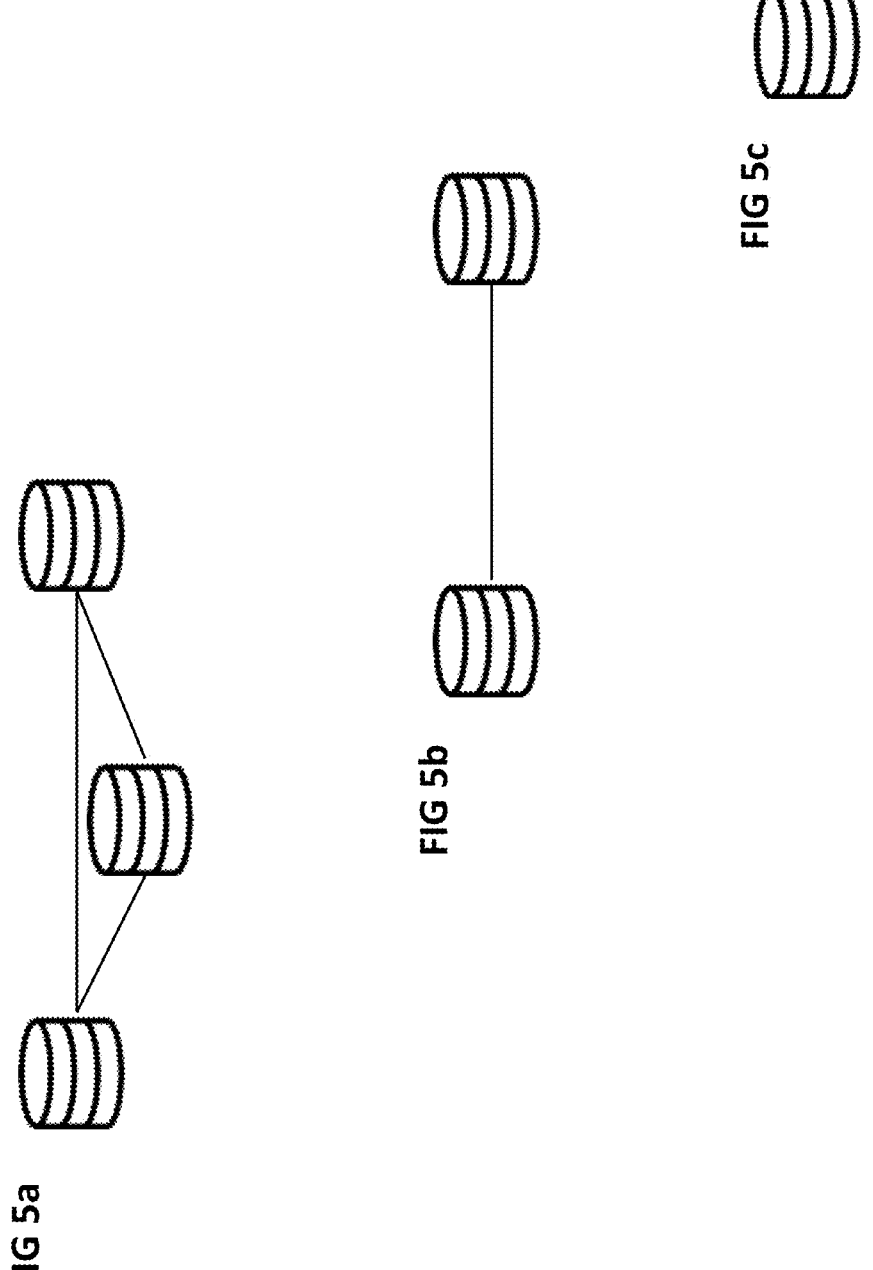
FIGS. 5*a*-5*c* show examples of how to store the components of the AI training data.

Thus, with the exemplary methods and computer systems described, the data can be stored in one or more connected databases. FIGS. 5*a*-5*c* show three exemplary possibilities of storing training data in one, two or three databases. The databases can be located on one, two or three physical storage devices. According to some embodiments, the data each remain in separate databases (FIG. 5*a*), but the system described here generates links between the databases, so that segmentations and classifications as well as semantic features can be unequivocally assigned to an image data set, image series, image and/or image element. Furthermore, there are unique links between segmentations and classifications and semantic features (FIG. 5*a*). In further embodiments, image data set, image series, image and/or image elements as well as segmentations and classifications are stored in a first database and there is a unique link to semantic features stored in a second database (FIG. 5*b*). In further embodiments, all data are stored in a common database (FIG. 5*c*). The linking of the elements of the image data, the contents of the findings reports and/or the segmentation and/or classification data can, e.g., be implemented in such a way that their memory addresses are linked with each other.

In the following, further embodiments of methods, computer systems and computer-program products according to the invention are described.

Figure 6:
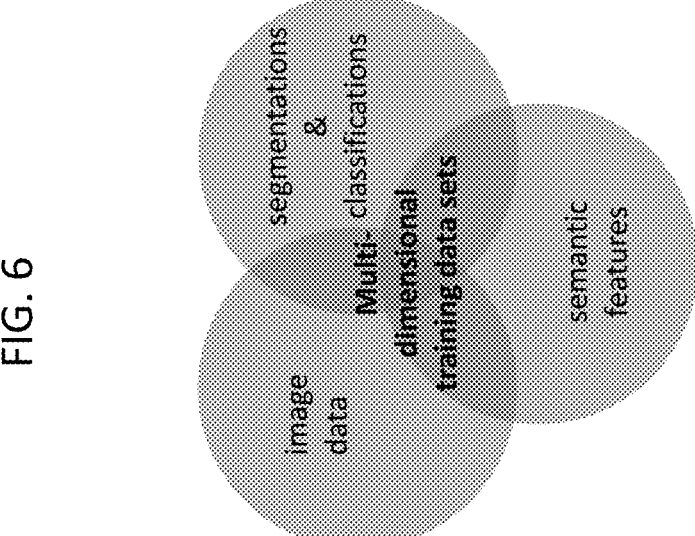
FIG. 6 illustrates the different options of combining the images-, findings report- and segmentation/classification-data.

In some embodiments, different collected data sets, such as image data, findings reports and/or segmentation and classification data, are combined to create diverse multidimensional training data sets. For illustration purposes, this is shown as an example in FIG. 6.

E.g., a combination of image data and segmentations and classifications results in conventional training data sets as they are typically used for the training of image-based algorithms.

Data sets that link image data and semantic features can be used to train image-based algorithms. So far, this does not correspond to common practice, as finding reports are usually not available in synoptic form.

Figure 7:
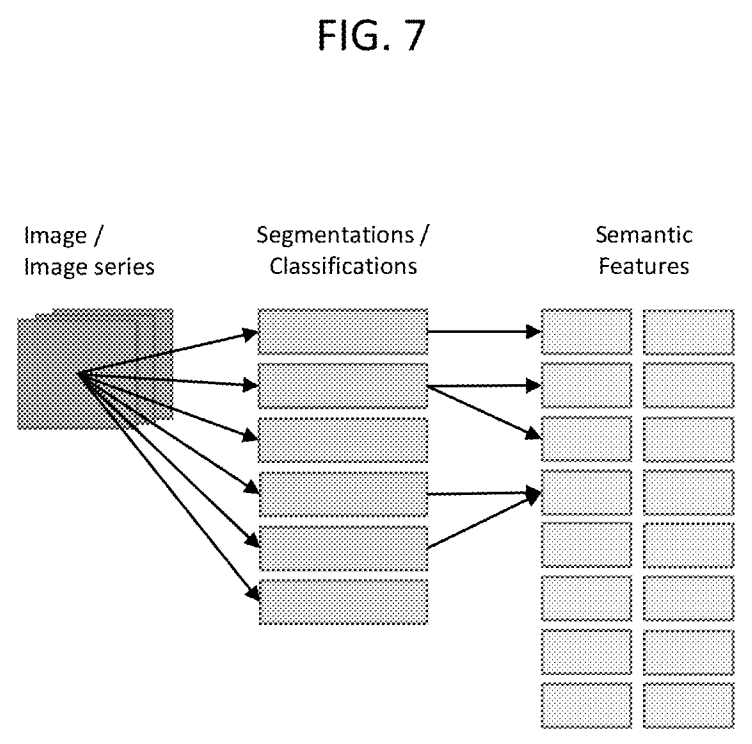

Data sets that combine image data, segmentation and classification information and semantic features contain all possible information about a medical image and represent the highest quality for training image-based algorithms, because the associated annotations can include segmentations, classifications and semantic features. FIG. 7 illustrates an example of how image data, segmentation/classification data and semantic features comprised in a findings report can be linked.

The data sets generated can also be used for other analytical purposes in the health sector (e.g. for monitoring the health status of patients or the population, for analyses of the functioning and effectiveness of the health care system, for evaluations of health economics, for determining reimbursement costs, for quality assurance, for clinical studies, for scientific evaluations in research and development, for collecting statistical data, for developing decision support and other medical assistance systems and other big data approaches).

We claim:

1. A computer-implemented method for medical imaging, the method comprising:
   a) receiving medical image data of a patient comprising medical image data elements;
   b) at least one of generating, editing, or receiving a synoptic structured medical findings report that summarizes individual medical findings and comprises a hierarchical tree-like data structure comprising machine-readable findings-report elements, wherein:
      the contents of the findings-report elements each comprise at least one semantic feature providing information about at least one of the patient or the received medical image data;
      the tree-like data structure reflects dependencies of the provided information; and
      each findings-report element and the contents of each findings-report element is assigned to a unique identifier of a database of identifiers each uniquely representing a medical semantic content of an individual medical finding;
   c) annotating the medical image data by linking one of the medical image data elements to the unique identifier to which the findings-report element is assigned, the contents of which provides information about the medical image data element;
   d) storing the annotated received medical image data as training data for an artificial intelligence (AI) algorithm; and
   e) causing the AI algorithm to be trained using the training data such that the AI algorithm can be used to generate a medical image of a second patient.

2. The method according to claim 1, wherein the unique identifiers comprise at least one of unique identification codes, or originate from a unique medical ontology.

3. The method according to claim 1, wherein the content of the findings-report element used for annotating the medical image data element comprises at least one of information in addition to or other than classification or segmentation information.

4. The method according to claim 1, further comprising:
   f) at least one of generating, editing, or receiving at least one of classification or segmentation data comprising at least one of classification or segmentation information associated with at least one of the received medical image data or the patient;
   g) further annotating the medical image data by linking the medical image data element with one or more classification or segmentation data;
   h) linking the classification or segmentation data with the findings-report element and the contents of the findings-report element;
   i) storing as second training data for the AI algorithm:
      i. the further annotated received medical image data; or
      ii. the linked classification or segmentation data and the findings-report element and the contents of the findings-report element; and
   j) causing the AI algorithm to be trained using the second training data such that the AI algorithm can be used to generate the medical image of the second patient.

5. The method according to claim 1, in which the linking of the medical image data element to the unique identifier is carried out while the findings-report element is generated or edited.

6. The method according to claim 1, wherein the AI algorithm is adapted to support at least one of radiological or pathological reporting and documentation.

7. The method according to claim 1, wherein the medical image of the second patient comprises an annotated medical image of the second patient.

8. A computer system for medical imaging, the computer system comprising:

memory comprising instructions; and processing circuitry configured to execute the instructions to:

a. receive medical image data of a patient comprising medical image data elements;

b. at least one of generate, edit, or receive a synoptic structured medical findings report comprising a hierarchical tree-like data structure which comprises machine-readable findings-report elements, wherein;

the contents of the findings-report elements each comprise at least one semantic feature providing information about at least one of the patient or the received medical image data;

the tree-like data structure reflects dependencies of the provided information; and each findings-report element and the contents of each findings-report element is assigned to a unique identifier of a database of identifiers each uniquely representing a medical semantic content of an individual medical finding;

c. annotate the received medical image data by linking one of the medical image data elements to the unique identifier to which the findings-report element is assigned, the contents of which provides information about the medical image data element;

d. store the annotated received medical image data as training data for an artificial intelligence (AI) algorithm; and e. cause the AI algorithm to be trained using the training data such that the AI algorithm can be used to generate a medical image of a second patient.

9. The computer system according to claim 8, wherein the unique identifiers comprise at least one of unique identification codes, or originate from a unique medical ontology.

10. The computer system according to claim 8, wherein the content of the findings-report element used for annotating the medical image data element comprises at least one of information in addition to or other than classification or segmentation information.

11. The computer system according to claim 8, wherein the medical image of the second patient comprises an annotated medical image of the second patient.

12. A computer system for medical imaging, the computer system comprising:

memory comprising instructions; and processing circuitry configured to execute the instructions to:

a. receive medical image data of a patient comprising medical image data elements;

b. at least one of generate, edit, or receive a synoptic structured medical findings report comprising a hierarchical tree-like data structure which comprises machine-readable findings-report elements, wherein:

the contents of the findings-report elements each comprise at least one semantic feature providing information about at least one of the patient or the received medical image data;

the tree-like data structure reflects dependencies of the provided information; and each findings-report element and the contents of each findings-report element is assigned to a unique identifier of a database of identifiers each uniquely representing a medical semantic content of an individual medical finding;

c. annotate the received medical image data by linking one of the medical image data elements with the unique identifier to which the findings-report element is assigned, the contents of which provides information about the medical image data element;

d. store the annotated received medical image data as first training data for an artificial intelligence (AI) algorithm;

e. at least one of generate, edit, or receive at least one of classification or segmentation data comprising segmentation or classification information associated with at least one of the received medical image data or the patient;

f. further annotate the received medical image data by linking the medical image data element with one of the classification or segmentation data;

g. link the classification or segmentation data with the findings-report element and the contents of the findings-report element;

h. store, as second training data for the AI algorithm, at least one of the further annotated received medical image data, or the linked classification or segmentation data and findings-report element and the contents of the findings-report element; and i. cause the AI algorithm to be trained using the first training data and the second training data such that the AI algorithm can be used to generate a medical image of a second patient.

13. The computer system according to claim 12, wherein the processing circuitry is configured to execute the instructions to link the medical image data element to the unique identifier while the findings-report element is generated or edited.

14. The computer system according to claim 12, wherein the AI algorithm is adapted to support at least one of radiological or pathological reporting and documentation.

15. A non-transitory computer-readable storage medium having instructions stored thereon that, when executed by processing circuitry, cause the processing circuitry to:

a) receive medical image data of a patient comprising medical image data elements;

b) at least one of generate, edit, or receive a synoptic structured medical findings report that summarizes individual medical findings and comprises a hierarchical tree-like data structure which comprises machine-readable findings-report elements, wherein:

the contents of the findings-report elements each comprise at least one semantic feature providing information about at least one of the patient or the received medical image data;

the tree-like data structure reflects dependencies of the provided information; and each findings-report element and the contents of each findings-report element is assigned to a unique identifier of a database of identifiers each uniquely representing a medical semantic content of an individual medical finding;

c) annotate the medical image data by linking one of the medical image data elements to the unique identifier to which the findings-report element is assigned, the contents of which provides information about the medical image data element;

d) store the annotated received medical image data as training data for an artificial intelligence (AI) algorithm; and e) cause the AI algorithm to be trained using the training data such that the AI algorithm can be used to generate a medical image of a second patient.

16. The non-transitory computer-readable storage medium according to claim 15, wherein the unique identifiers comprise at least one of unique identification codes, or originate from a unique medical ontology.

17. The non-transitory computer-readable storage medium according to claim 15, wherein the content of the findings-report element used for annotating the medical image data element at least one of information in addition to or other than classification or segmentation information.

18. The non-transitory computer-readable storage medium according to claim 15, wherein the instructions, when executed by the processing circuitry, cause the processing circuitry to:

f) at least one of generate, edit, or receive at least one of classification or segmentation data comprising at least one of classification or segmentation information associated with at least one of the received medical image data or the patient;

g) further annotate the medical image data by linking the medical image data element with one of the classification or segmentation data;

h) link the classification or segmentation data with the findings-report element and the contents of the findings-report element;

i) store as second training data for the AI algorithm:

i. the further annotated received medical image data; or ii. the linked classification or segmentation data and the findings-report element and the contents of the findings-report element; and j) cause the AI algorithm to be trained using the second training data such that the AI algorithm can be used to generate the medical image of the second patient.

19. The non-transitory computer-readable storage medium according to claim 15, in which the linking of one of the medical image data elements to the unique identifier is carried out while the findings-report element is generated or edited.

20. The non-transitory computer-readable storage medium according to claim 15, wherein the medical image of the second patient comprises an annotated medical image of the second patient.

* * * * *